(12) United States Patent
Yokoyama

(10) Patent No.: US 8,906,692 B2
(45) Date of Patent: Dec. 9, 2014

(54) INSTRUMENT AND METHOD FOR ANALYSIS OF MANNOSE 6-PHOSPHATE

(75) Inventor: Tetsuo Yokoyama, Hyogo (JP)

(73) Assignee: JCR Pharmaceuticals Co., Ltd.

( * ) Notice: Subject to any disclaimer, the term of this patent is extended or adjusted under 35 U.S.C. 154(b) by 0 days.

(21) Appl. No.: 14/007,977

(22) PCT Filed: Mar. 26, 2012

(86) PCT No.: PCT/JP2012/057693
§ 371 (c)(1),
(2), (4) Date: Oct. 29, 2013

(87) PCT Pub. No.: WO2012/133269
PCT Pub. Date: Oct. 4, 2012

(65) Prior Publication Data
US 2014/0051175 A1  Feb. 20, 2014

(30) Foreign Application Priority Data

Mar. 29, 2011  (JP) ................. 2011-073630

(51) Int. Cl.
| | | |
|---|---|---|
| G01N 30/02 | (2006.01) | |
| G01N 21/64 | (2006.01) | |
| G01N 30/30 | (2006.01) | |
| G01N 30/74 | (2006.01) | |
| G01N 30/84 | (2006.01) | |
| G01N 30/88 | (2006.01) | |

(52) U.S. Cl.
CPC ............ *G01N 21/6486* (2013.01); *G01N 30/30* (2013.01); *G01N 2030/3007* (2013.01); *G01N 30/74* (2013.01); *G01N 2030/8435* (2013.01); *G01N 2030/8836* (2013.01); *G01N 30/88* (2013.01); *G01N 30/84* (2013.01)
USPC ............... 436/94; 436/89; 436/161; 436/164; 436/172; 422/70; 422/82.08; 73/61.52; 73/61.53; 73/61.55; 73/61.56

(58) Field of Classification Search
USPC ............... 436/86, 89, 94, 147, 161, 164, 172, 436/174, 175; 422/68.1, 70, 82.05, 82.08; 210/656, 198.2; 73/61.52, 61.53, 73/61.55, 61.56
See application file for complete search history.

(56) References Cited

U.S. PATENT DOCUMENTS

| | | |
|---|---|---|
| 8,093,364 B2 | 1/2012 | Gagnon |
| 8,522,603 B2 | 9/2013 | Yokoyama |

(Continued)

FOREIGN PATENT DOCUMENTS

| | | |
|---|---|---|
| JP | 2005-278597 A | 10/2005 |
| JP | 2006184131 A | 7/2006 |

(Continued)

OTHER PUBLICATIONS

Pickering. LC-GC, vol. 6, No. 11, Nov. 1988, pp. 994 and 996-997.*

(Continued)

*Primary Examiner* — Maureen Wallenhorst
(74) *Attorney, Agent, or Firm* — Millen, White, Zelano & Branigan, P.C.

(57) ABSTRACT

Disclosed are an apparatus and method for separation analysis of mannose-6-phosphate (M6P) by post-column fluorescence detection method. The apparatus is based on chromatography, and includes a column with a solid phase having affinity for phosphate, a flow path for the eluate, a heater installed on the flow path for M6P and a basic amino acid to react by heating the eluate in the flow path, and a fluorescence detector installed downstream of the heater for continuously irradiating the eluate with excitation light and measuring the intensity of the emission, and may include in the flow path a supply channel for addition of a basic amino acid between the column and the heater. The method is characterized in that it uses the apparatus and a second mobile phase consisting of a second buffer containing phosphate of predetermined concentration and adjusted to a predetermined pH.

14 Claims, 2 Drawing Sheets

(56) References Cited

U.S. PATENT DOCUMENTS

| | | |
|---|---|---|
| 2009/0186396 A1 | 7/2009 | Gagnon |
| 2009/0187005 A1 | 7/2009 | Gagnon |
| 2010/0035328 A1 | 2/2010 | Oki et al. |
| 2010/0229634 A1 | 9/2010 | Yokoyama |
| 2012/0077961 A1 | 3/2012 | Gagnon |

FOREIGN PATENT DOCUMENTS

| | | |
|---|---|---|
| JP | 2008-088102 A | 4/2008 |
| JP | 2008185373 A | 8/2008 |
| JP | 2008245550 A | 10/2008 |
| JP | 2010-175418 A | 8/2010 |
| JP | 2010237199 A | 10/2010 |
| WO | 2009092010 A1 | 7/2009 |

OTHER PUBLICATIONS

Sawada et al. Analytical Biochemistry, vol. 314, 2003, pp. 63-69.*
English translation Abstract for JP 58-216953 dated Dec. 16, 1983.
English translation Abstract for JP 61-025059 dated Feb. 3, 1986.
"ICSC Boric Acid" http://www.inchem.org/documents/icsc/icsc/eics0991.htm [Oct. 1994], 3 pages.
Hirohisa Mikami et al. "Post-Column Fluorometric Detection of Reducing Sugars in High Performance Liquid Chromatography Using Arginine" Bunseki Kagaku, vol. 32, [1983], pp. E207-E2010.
International Search Report from PCT/JP2012/057693 dated Jun. 19, 2012.

* cited by examiner

INSTRUMENT AND METHOD FOR ANALYSIS OF MANNOSE 6-PHOSPHATE

TECHNICAL FIELD

The present invention relates to an apparatus for analysis of mannose-6-phosphate (M6P) by the post-column fluorescence detection method and an improvement of the method for analysis using the apparatus.

BACKGROUND ART

A method for analysis of reducing sugars is known which comprises subjecting a sample containing reducing sugars to liquid chromatography using as a mobile phase an aqueous solution containing boric acid; adding to the eluate, in the flow path, a boric acid aqueous solution containing a basic amino acid such as arginine; and letting it to react with the reducing sugars by heating, then cooling the reaction solution, and measuring its absorbance, or intensity of fluorescence from it under irradiation with excitation light (Patent Document 1). The apparatus used in the method comprises an extended flow path from a column, to which flow path is connected a supply channel for a boric acid aqueous solution containing a basic amino acid, and are attached a heater, a cooling device, an excitation light irradiator, and a device for measuring fluorescence intensity or the like. In this method, the supply channel is indispensable for addition of a boric acid aqueous solution containing a basic amino acid to the eluate from the liquid chromatography.

Further, an improved type of the above method is known, which comprises subjecting a sample containing reducing sugars to liquid chromatography using a mobile phase containing boric acid and a reagent basic amino acid, such as arginine, heating the eluate in the flow path to allow the reagent to react with the reducing sugars, then cooling the reaction solution, and measuring its absorbance, or the intensity of fluorescence under irradiation of the reaction solution with excitation light (Patent Document 2). In this method, as a boric acid aqueous solution containing a basic amino acid is employed as the mobile phase for liquid chromatography, there is no need for providing a supply channel for later addition of a boric acid aqueous solution containing a basic amino acid. These methods for analysis of reducing sugars are called post-column fluorescence detection/boric acid complex anion exchange method.

For detection of reducing sugars eluted from a column, both of the above methods for analysis of reducing sugars utilize production of potent fluorogenic derivatives by heat-reaction of reducing sugars with a basic amino acid, such as arginine in the presence of boric acid (Non-patent Document 1). The fluorogenic derivatives are melanoidins, brown compounds which are produced by a heat-reaction between reducing sugars and a basic amino acid, which is an amino compound (Maillard reaction). They emit light at the wavelength of 430 nm when irradiated with excitation light at the wavelength of 320 nm. For separation of reducing sugars by a column, these methods for analysis of reducing sugars utilize the properties of reducing sugars that they readily bind to boric acid to form an anionic complex ion and this anionic complex ion is retained by an anion exchanger column.

In the post-column fluorescence detection/boric acid complex anion exchange method, an aqueous solution (pH 7-10) is employed, as a mobile phase, which contains a basic amino acid at a concentration of 0.01-5% and boric acid at a concentration of 0.05-0.5 M. Those amino acids which can be employed above are arginine, lysine, histidine, and the like.

As any of such basic amino acids, whether it is D-, L-, or DL-form, equivalently produces melanoidins, its enantiomers or racemic mixtures can equally be used in the reaction. Further, it has recently been known to separate sugars using a gradient created in the mobile phase for liquid chromatography based on 0.1 M borate buffer and 0.4 M borate buffer (Patent Documents 3 and 4). Furthermore, a method for separation of sugars utilizing a gradient of an inorganic salt concentration has been developed, in which the concentration of boric acid in the borate buffer used as the mobile phase is set at 50-150 mM and an inorganic salt such as sodium chloride is added to the buffer (Patent Document 5). According to this method, clogging of the piping with precipitating boric acid can be prevented, for the mobile phase contains boric acid only at a low concentration.

In the conventional post-column fluorescence detection/boric acid complex anion exchange method, elution of a sample in liquid chromatography is carried out at temperatures from room temperature to 70° C., and the heat reaction (Maillard reaction) is allowed to proceed at 140-180° C. (Patent Document 2). Since the reaction and elution are performed at such high temperatures and at high boric acid concentrations, such phenomena occur as thermal expansion of the mobile phase and convection in the mobile phase. These phenomena can cause noises in the fluorescence detected by a fluorescence detector in the post-column fluorescence detection/boric acid complex anion exchange method, and can lower the sensitivity of detection. Thus, in the analysis of reducing sugars by such methods, particularly in their quantitative analysis, it has been required to compensate the result of detection by using dedicated software.

Reducing sugars which can be analyzed using the post-column fluorescence detection/boric acid complex anion exchange method are those which undergo the Maillard reaction with basic amino acids, including monosaccharides such as glucose, mannose, galactose, fructose, and rhamnose; oligosaccharides such as maltose and maltotriose; amino sugars such as glucosamine, and galactosamine; and uronic acids such as glucuronic acid.

Examples of analytes of this method include reducing sugars derived from sugar chains of glycoproteins. Reducing sugars as components of sugar chains of glycoproteins include monosaccharides such as mannose, galactose, and fucose; amino sugars such as galactosamine. Such sugar chains sometimes contain mannose-6-phosphate (M6P). M6P in sugar chains is indispensable for a glycoprotein to bind to the mannose-6-phosphate receptor, a membrane receptor.

Some of the enzymes used in the enzyme replacement therapy for lysosomal diseases require M6P in their sugar chains for them to exhibit their pharmacological effect. The reason for this is as follows: those enzymes bind to the mannose-6-phosphate receptor on the cells via M6P in their sugar chains, and then they are taken into endoplasmic reticula in the cells by endocytosis, which then, by fusion with lysosomes, carry them into the lysosomes, and exhibit their pharmacological effect by decomposing their substrate in the lysosomes. Therefore, if they lack M6P, they even cannot be taken in by the cells. Examples of such enzymes include lysosomal acid lipase, acid sphingomyelinase, acid α-glucosidase (acid maltase), and N-acetylgalactosamine4-sulfatase, and these enzymes produced by the recombinant technology are useful in the enzyme replacement therapy for Wolman disease, Niemann-Pick disease, Pompe disease and Maroteaux-Lamy syndrome, respectively.

When it is orally ingested, boric acid, which is used in post-column fluorescence detection/boric acid complex anion exchange method, causes, abdominal pain, cramps, diarrhea, nausea, vomiting, exanthema, and dizziness, and also may cause dermatitis when it is repeatedly or chronically brought into contact with the skin. Further, animal studies have shown that boric acid may have a reproductively toxic effect on humans (Non-patent Document 2). Therefore, the above method poses a substantial impact on the environment due to the resulting waste fluid containing boric acid with such a toxicity.

PRIOR ART DOCUMENTS

Patent Documents

[Patent Document 1] Japanese Patent Application Publication No. S58-216953
[Patent Document 2] Japanese Patent Application Publication No. S61-25059
[Patent Document 3] Japanese Patent Application Publication No. 2006-184131
[Patent Document 4] Japanese Patent Application Publication No. 2008-425550
[Patent Document 5] Japanese Patent Application Publication No. 2010-237199

Non-Patent Documents

[Non-patent Document 1] Mikami H. et. al., Bunseki Kagaku (1983) 32, E207
[Non-patent Document 2] International Chemical Safety Cards (ISCS) International English version, International Labor Organization (updated on Nov. 30, 2004).

DISCLOSURE OF THE INVENTION

Problem to be Solved by the Invention

Against the above-mentioned background, an objective of the present invention is to provide a method which enables detection of mannose-6-phosphate in reducing sugars, without employing boric acid in a post-column fluoresce detection method. Another objective of the present invention is to remove noises in the fluorescence detected by the fluorescence detector and thereby to improve detection sensitivity in the post-column fluorescence detection method, by installing a back-pressure generator in the flow path of the separation analysis apparatus used in the detection method.

Means to Solve the Problem

In a study for the above-mentioned objectives, the inventor found that mannose-6-phosphate in reducing sugars can be separated and detected without using boric acid, but by using, instead of a boric acid aqueous solution, a Tris buffer and a Tris buffer containing phosphate in the mobile phase, and employing hydroxyapatite column chromatography instead of anionic exchanger column chromatography as the liquid chromatography. The present invention was completed based on the findings.

Thus, the present provides what follows.

1. An apparatus for separation analysis of mannose-6-phosphate contained in a sample using column chromatography, which comprises a column with a solid phase having affinity for phosphate, a flow path for the eluate from the column, a heater for heating the eluate in the flow path to cause mannose-6-phosphate and a basic amino acid contained in the eluate to react, and a fluorescence detector installed in the flow path downstream of the heater for continuously irradiating the eluate with excitation light and measuring the intensity of fluorescence emitted from the eluate; and which may further comprise in the flow path a supply channel for addition of a basic amino acid between the column and the heater.

2. The apparatus for separation analysis according to 1 above, wherein a cooling device is further installed in the flow path between the heater and the fluorescence detector.

3. The apparatus for separation analysis according to 1 or 2 above, wherein a back-pressure generator is further installed in the flow path between the heater and the fluorescence detector.

4. The apparatus for separation analysis according to 3 above, wherein the cooling device is installed between the heater and the back-pressure generator.

5. The apparatus for separation analysis according to one of 1 to 4 above, wherein the solid phase is selected from the group consisting of hydroxyapatite, fluoroxyapatite, and a mixture thereof.

6. A method for separation analysis of mannose-6-phosphate contained in a sample using the apparatus according to one of 1 to 5 above, comprising
loading the sample onto the column,
washing the column by passing through the column a sufficient amount of a first mobile phase consisting of a first buffer adjusted to a predetermined pH,
eluting mannose-6-phosphate by continuously supplying, at a predetermined flow rate, a second mobile phase consisting of a second buffer containing a predetermined concentration of phosphate and adjusted to a predetermined pH,
continuously leading the eluate from the column to the flow path,
continuously adding, at a predetermined flow rate, a solution containing at least one basic amino acid to the eluate in the flow path to form a mixture solution,
letting the mixture solution pass through the heater at a predetermined temperature over a predetermined length of time to heat the mixture solution, and
measuring and recording the intensity of fluorescence emitted from the mixture solution under irradiation with predetermined excitation light by subjecting the heated mixture solution to the fluorescence analysis device.

7. The method for separation analysis of mannose-6-phosphate contained in a sample using the apparatus according to one of 1 to 5 above, comprising
loading a solution of the sample containing mannose-6-phosphate onto the column,
washing the column by passing through the column a sufficient amount of a first mobile phase consisting of a first buffer containing a predetermined concentration of at least one basic amino acid and adjusted to a predetermined pH,
eluting mannose-6-phosphate by continuously supplying, at a predetermined flow rate, a second mobile phase consisting of a second buffer containing at least one basic amino acid and a predetermined concentration of phosphate and adjusted to a predetermined pH,
continuously leading the eluate from the column to the flow path,
letting the eluate pass through the heater at a predetermined temperature over a predetermined length of time to heat the eluate, and
measuring and recording the intensity of fluorescence emitted from the eluate under irradiation with predetermined excitation light by subjecting the heated eluate to the fluorescence analysis device.

8. The method according to 6 or 7 above, wherein the pH of the first mobile phase is 5.5 to 9.5 and the pH of the second mobile phase is 5.5 to 9.5.

9. The method according to 8 above, wherein
the first buffer is selected from the group consisting of Tris buffer, Good buffer, acetate buffer, citrate buffer, citrate-phosphate buffer, phosphate buffer, glycine buffer, and carbonate buffer, or from a mixture solution of at least two of these,
the second buffer is selected from the group consisting of Tris buffer, Good buffer, acetate buffer, citrate buffer, citrate-phosphate buffer, phosphate buffer, glycine buffer, and carbonate buffer, or from a mixture solution of at least two of these.

10. The method according to one of 6 to 9 above, wherein the concentration of the phosphate contained in the second mobile phase is 15-50 mM.

Effect of the Invention

In the post-column fluorescence detection method, the present invention enables separation analysis of mannose-6-phosphate (M6P) in reducing sugars without using boric acid, which has been used conventionally. Therefore, according to the present invention, unlike the conventional method, boric acid-containing waste fluid is not produced and thus a facility for treating it, such as a processing tank, becomes unnecessary. Thus, the present invention has an economic advantage and is also favorable to the environment.

MODE FOR CARRYING OUT THE INVENTION

Figure 1:
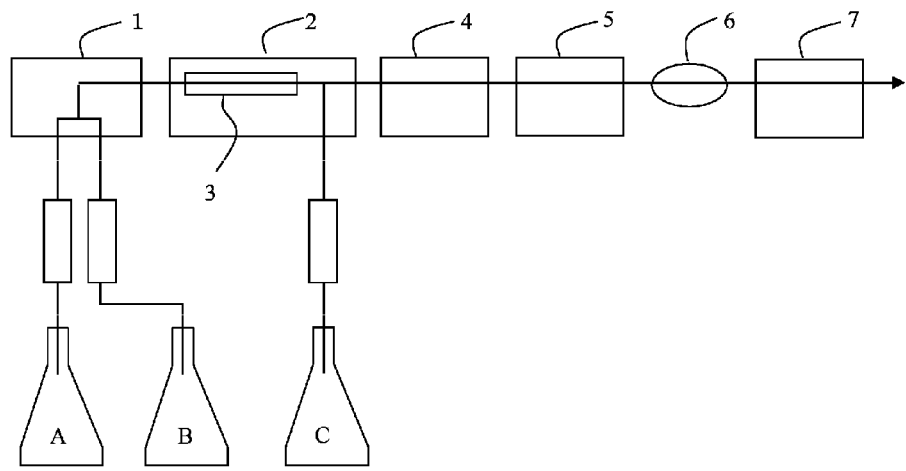
FIG. 1 is a schematic illustration of the arrangement and the flow path of the apparatus in the example.

In the present invention, the term "post-column fluorescence detection method" means a method which comprises subjecting a sample containing reducing sugars to liquid chromatography, eluting it, heating the eluate with a reagent basic amino acid such as arginine to allow the reagent and the sugars to react (heat reaction), cooling it, and measuring the absorbance, or the intensity of fluorescence emitted from the reaction solution under irradiation with excitation light.

In the present invention, the term "solid phase having affinity for phosphate" means a carrier which can capture and retain phosphate in a solution under a certain condition, and preferably hydroxyapatite, fluoroxyapatite, or a carrier to which a hydrated metal oxide is bound, more preferably hydroxyapatite, or fluoroxyapatite, and most preferably hydroxyapatite.

As it is relatively inexpensive, employment of hydroxyapatite as the above solid phase is preferred for reduction of costs of the analysis.

In the term "carrier to which a hydrated metal oxide is bound", examples of a "carrier" include, but are not limited to, polysaccharides such as cellulose, and dextran. And a hydrated metal oxide may be selected from the group consisting of titanium oxide, aluminium oxide, yttrium iron garnet, yttrium aluminium garnet, yttrium aluminium gallium garnet, ferric oxide, gallium oxide, yttrium oxide, vanadium oxide, zirconium oxide, iron titanate, iron aluminate, calcium titanate, sodium titanate, zirconium aluminate, goethite, gibbsite, bayerite, boehmite, ilmenite, ilmenorutile, pseudorutile, rutile, brookite, pseudobrookite, geikielite, pyrophanite, ecandrewsite, melanostibite, armalcolite, srilankite, and anatase, and is preferably titanium oxide, aluminium oxide, and yttrium iron garnet, and most preferably titanium oxide. A carrier to which titanium oxide is bound is on the market and thus available (Titansphere (GL Science Inc.)).

In the present invention, the term "fluoroxyapatate" means a fluorinated calcium phosphate represented by the chemical formula $Ca_5(PO_4)_3F$. Fluoroxyapatite can be produced by replacing hydroxyl groups of hydroxyapatite with fluorine. A product in which hydroxyl groups of hydroxyapatite are almost completely fluorinated is on the market and thus available (CFT Type II 40 micrometer (Bio-Rad Laboratories)).

In the present invention, buffers that may be used as the first buffer and the second buffer are preferably selected from the group consisting of Tris buffer, Good buffer, acetate buffer, citrate buffer, citrate-phosphate buffer, phosphate buffer, glycine buffer, and carbonate buffer, or from a mixture solution of at least two of these. In the above, Good buffer means a group of ampholyte ion buffers in general including MES, Bis-tris, ADA, Bis-tris propane, PIPES, ACES, MOPSO, cholamine chloride, BES, MOPS, TES, HEPES, DIPSO, TAPSO, POPSO, HEPPSO, HEPPS(EPPS), Tricine, glycinamide, Bicine, TAPS, CHES, CAPSO, CAPS and their mixture solution. Among these buffers, more preferred as the first and the second buffers are Tris buffer, HEPES buffer, and MES buffer, and most preferred is Tris buffer. Herein, Tris buffer means a buffer which is a solution of tris(hydroxymethyl)aminomethane adjusted to a certain pH.

In the present invention, the pH of the first and the second buffers are preferably 5.5-9.5, and more preferably 7.0-8.5. When Tris buffer is used as the first and the second buffers, its pH is preferably 7.2-9.4, and its concentration [the concentration of tris(hydroxymethyl)aminomethane] is preferably 15-25 mM, and more preferably about 20 mM. If hydroxyapatite is used, however, the pH of the first and the second buffers is preferably 6.5-9.5, and more preferably 7.0-8.5, regardless of which of the specific buffers is employed.

In the present invention, though there is no particular limitation as to the concentration of phosphate added to the second buffer so long as it enables elution of carrier-retained mannose-6-phosphate from the carrier, phosphate is added so that its concentration of not less than 10 mM in general, and most commonly 15-50 mM, is achieved.

In the present invention, the conditions for performing the post-column fluorescence detection method, such as flow rate of the mobile phases, temperature of the column, the reagent and its concentration in the reagent solution, rate of injection of the reagent solution, and temperature in the heater, may be set or chosen without any particular limitation so long as they allow separate analysis of mannose-6-phosphate. For example, the conditions set forth in Table 1 and Table 2 may be employed (Method I and Method II).

TABLE 1

Conditions for post-column fluorescence detection/boric acid
complex anion exchange method (Method I and Method II)

|  | Method I | Method II |
|---|---|---|
| Detection method (Fluorescence) | Excitation light: 320 nm Fluorescence: 430 nm | Excitation light: 320 nm Fluorescence: 430 nm |
| Solution A | 20 mM Tris buffer (pH 7.2) | 20 mM HEPES (pH 7.5) |
| Solution B | 20 mM Tris buffer (pH 7.2), 20 mM phosphate | 20 mM HEPES (pH 7.5), 20 mM phosphate |
| Flow rate of mobile phase | 0.3 mL/min | 0.3 mL/min |
| Column temperature | 25° C. | 25° C. |
| Reagent solution | 20 mM Tris buffer (pH 7.2), 3 w/v % DL-arginine | 20 mM HEPES (pH 7.5) 3 w/v % DL-arginine |
| Injection rate of reagent solution | 0.2 mL/min | 0.2 mL/min |
| Temperature in the heater | 150° C. | 150° C. |

TABLE 2

Ratio of solution B in mobile phase and time
for passing mobile phase through column

|  | Method I | | Method II | |
|---|---|---|---|---|
| Mobile phase | Time after starting analysis (min) | Solution B (v/v %) | Time after starting analysis (min) | Solution B (v/v %) |
| First mobile phase | 0-30 | 0 | 0-30 | 0 |
| Second mobile phase | 30-60 | from 0 to 100 | 30-60 | from 0 to 100 |
| Second mobile phase | 60-70 | 100 | 60-70 | 100 |
| — | 70 and thereafter | 0 | 70 and thereafter | 0 |

In the present invention, both solution A and solution B, which are used as mobile phases alone or in the form of their mixture, are aqueous solutions. When increasing the ratio of solution B, the ratio may be increased continuously or discontinuously, though it may preferably be increased continuously, and particularly preferably in a linear fashion (i.e., at a constant rate and continuously). This increase of the ratio of solution B may be continued until the analyte, mannose-6-phosphate, is eluted.

In the present invention, the term "first mobile phase" means the mobile phase, which is used first when starting chromatography after loading a sample, and it is a washing solution for washing and removing contaminants while keeping mannose-6-phosphate bound to the column. In Table 2, the first mobile phase consists of solution A. The term "second mobile phase" refers to a mobile phase which is passed through the column to elute mannose-6-phosphate from the column (in Table 2, a solution in which the ratio of solution B is increased from 0 v/v %) after the first mobile phase is passed through the column. When the plain term "mobile phase" is used, it indicates both the first mobile phase and the second mobile phase without distinction.

The flow rate of the mobile phase should be properly adjusted depending on such factors as the apparatus for analysis employed and characteristics of the analyte so that a clear analytical result can be obtained. Though it is adjusted generally to 0.1-1 mL/min, it may be adjusted to less than 0.1 mL/min or more than 1 mL/min, depending on the characteristic of an apparatus employed.

In the column chromatography according to the present invention, the elution process may be performed at room temperature, but more consistent results can be obtained by installing the column in a thermostatic chamber (column thermostatic chamber) to keep the temperature constant, at 25° C., for example.

Though there is no particular limitation as to which basic amino acid is employed in the present invention, preferred is arginine, lysine or histidine, and particularly preferred is arginine. As to basic amino acids, one of them may be used alone, or two or more of them in the form of a mixture. Further, a basic amino acid may be added by injecting, as a reagent solution, an aqueous solution containing the basic amino acid into the eluate flowing in the flow path from the column. In this case, the rate of injection of the basic amino acid may be set as desired so long as it is kept constant during a cycle of analysis. It is injected so that its concentration after it is mixed with the eluate in the flow path from the column (final concentration) is 0.1-2 w/v % in general, and preferably 0.5-1.8 w/v %, and more preferably 1.0-1.5 w/v %. As an aqueous solution containing a basic amino acid, a buffer containing it is preferably used, for example. In this case, the type of the buffer, its concentration and pH may be the same as, or somewhat deferent from, those of the buffer of the mobile phase.

Further, instead of adding a basic amino acid later as a reagent solution to the eluate flowing in the flow path from the column, the basic amino acid may be dissolved in a mobile phase in advance at a predetermined concentration. This allows elimination of a supply channel, which is indispensable if a reagent solution containing the basic amino acid is added later to the eluate. In that case, the concentration of the basic amino acid in the mobile phase may be adjusted 0.1-2 w/v %, and is adjusted preferably to 0.5-1.8 w/v %, and more preferably 1.0-1.5 w/v %.

In the present invention, the reaction temperature at which the reducing sugars and a basic amino acid contained in the eluate from the column (if a basic amino acid is later added to the eluate from the column, the eluate after receiving it) are allowed to react by heat (heat reaction) in the heater, may be 140-180° C., and is preferably about 150° C. The reaction occurring here is the Maillard reaction, by which reducing groups in the sugar molecules and a basic amino acid react to produce brown compounds (melanoidins). The heater is an apparatus having a heating zone in which to heat the solution in the flow path for a predetermined length of time to a predetermined temperature, and thus any apparatus having such a heating zone may be employed as a heater, without particular limitation. Though there is no particular limitation as to the duration of heating in the heater so long as it is sufficient for causing the Maillard reaction to take place, it is generally set at 1-20 min.

In the present invention, in order to further reduce noises in the fluorescence detected by a fluorescence detector, the eluate having undergone the heat reaction is preferably cooled by passing it through a cooling device. Though there is no particular limitation as to the temperature of the eluate after cooling so long as it does not affect the measurement of fluorescence intensity, it is preferably 15-70° C. Cooling here may be performed, e.g., by air-cooling or water-cooling of the flow path by the cooling device. Air-cooling may be performed by blowing air toward the flow path with a fan. For water-cooling, tap water may be used directly. Further, cooling may be performed by passing the flow path through a column thermostatic chamber. As a column thermostatic chamber can be set at a constant temperature, e.g., 25° C., it is possible to lower the temperature of the eluant after the heat reaction, by passing the flow path through a column thermostatic chamber.

A back-pressure generator, which may be employed in the present invention, is a device installed in the flow path to increase the pressure of the solution (back pressure) in the flow path on its upstream side. A back-pressure generator, when employed, has an effect to reduce noises in the fluorescence detected by a fluorescence detector in the post-column detection method. Therefore, it is particularly preferred to install a back-pressure generator when improved accuracy in the analysis of mannose-6-phosphate is required. Any back-pressure generator may be employed without particular limitation, so long as it can create back pressure. Back pressure may be created, e.g., by narrowing the flow path in a back-pressure generator. A back-pressure generator on the market [1/16. flange-type unit (4×1.3 cm), mfd by SSI, BACK PRESSURE REGULATOR ASSEMBLY, WITH P-763 (100 PSI) CARTRIDGE, No U-607, mfd by Upchurch Scientific] can be suitably used as a back-pressure generator in the present invention. Each of these back-pressure regulators is a device which is used to generate a constant back pressure in the detector by attaching it generally to the detector outlet.

In the present invention, a back-pressure generator is installed in the flow path between a heater and a fluorescence detector. Where a cooling device is installed downstream of a heater, the back pressure generator is installed between the cooling device and the fluorescence detector.

The sugars that can be analyzed by the present invention include, in addition to mannose-6-phosphate, polysaccharides containing mannose-6-phosphate. "Polysaccharides" as referred to here includes disaccharides and oligosaccharides. Furthermore other phosphorylated sugars than mannose-6-phosphate can also be analyzed. Sugars to be analyzed are provided in the form of a sample solution, i.e., a solution prepared by dissolving them in a predetermined solution in such a manner that their concentration falls within a predetermined range. The predetermined solution employed above is an aqueous solution, preferably purified water or a solution with the same composition as the first mobile phase.

EXAMPLES

The present invention is described in further detail below with reference to examples. However, it is not intended that the present invention be limited to those examples.
[Preparation of M6P Standard Solution]

M6P Standard Stock Solution was prepared by dissolving 10 mg of mannose-6-phosphate sodium salt in purified water and adjusting the volume to 5 mL. Mannose-6-phosphate Standard Solution (M6P Standard Solution) was prepared by diluting the M6P Standard Stock Solution 20-fold with purified water. Three hundred mg of D(+)-mannose, 100 mg of L(−)-fucose, and 300 mg of D(+)-galactose were dissolved in purified water and the volume was adjusted to 100 mL. This solution was diluted 20-fold with purified water to prepare Neutral Reducing Sugar Mixture Standard Solution. Reducing Sugar Standard Solution was prepared by mixing 18 ml of the Neutral Reducing Sugar Mixture Standard Solution and 2.5 mL of M6P Standard Solution, and adding purified water to this to adjust the its volume to 50 mL.
[Preparation of Solutions for Mobile Phases]

To purified water was added 2.4 g of tris(hydroxymethyl) aminomethane and dissolved, and after the pH of this solution was adjusted to 7.2 with 2 N hydrochloric acid, purified water was added to make the total volume 1000 mL, and this solution was suction filtered through a 0.22 μm membrane filter. The solution thus obtained was designated Solution A (20 mM Tris buffer (pH 7.2)). Further, to purified water were added 2.4 g of Tris(hydroxymethyl)aminomethane and 3.1 g of sodium dihydrogenphosphate dihydrate, and dissolved, and after the pH of this solution was adjusted to 7.2 with 2 N hydrochloric acid, purified water was added to make the total volume 1000 mL, and this solution was suction filtered through a 0.22 μm membrane filter. The solution thus obtained was designated Solution B (20 mM Tris buffer-20 mM phosphate solution (pH 9.0)).
[Preparation of Reagent Solution]

To Solution A was added 30 g of L-arginine and dissolved, and after the total volume was adjusted to 1000 mL, suction filtered through a 0.22 μm membrane filter. The solution thus obtained was designated Reagent Solution.
[Analysis of Mannose-6-Phosphate by Post-Column Fluorescence Detection Method (1)]
(1) Apparatus A CHT-I column (5.0 mm I.D.×50 mm, substrate: CTH ceramic hydroxyapatite Type I 40 μm, Bio-Rad Laboratories), which is a hydroxyapatite column, was attached to Shimazu HPLC System LC-20A (reducing sugar analysis system, Shimazu Corp.), and the column was placed in a thermostatic chamber (column thermostatic chamber) at 25° C. A heat Block (ALB-221, mfd by Asahi Techno Glass) was set as a heater downstream of the column outlet. A cooling bath (a bath filled with tap water at room temperature) was installed downstream of the Heat Block, further downstream of which was installed Back-Pressure Regulator (M&S Instruments Inc., U-607) as a back-pressure generator. Further downstream of this, a fluorescence detector was installed for detection of fluorescence with the wavelength at 430 nm while irradiating the solution coming out of Back-Pressure Regulator with ultraviolet light having the wavelength at 320 nm. The arrangement of the apparatus and the flow paths are illustrated in FIG. 1.
(2) Operation Procedures Solutions A and B were set on the autosampler of the reducing sugar analysis system, and the apparatus was arranged so that Reagent Solution would be supplied downstream of the column outlet (and upstream of the Heat Block) (See FIG. 1). After the column was equilibrated with the first mobile phase consisting of Solution A, M6P Standard Solution was loaded onto the column.

After M6P Standard Solution was loaded onto the columns, the first mobile phase was passed through the column at the flow rate of 0.3 mL/min for 30 min, and then the volume ratio of Solution B was increased up to 100% in a linear fashion over 30 min at the same flow rate, then after Solution B was passed at the same flow rate for further 10 min, Solution A was passed at the same flow rate for 20 min. Meanwhile, Reagent Solution was supplied to the flow path at the flow rate of 0.2 mL/min so that it would mix with the eluate coming out of the column downstream of the column outlet. Therefore, the concentration of arginine in the mixture solution was 3×0.2/(0.3+0.2)=1.2 w/v %. Table 3 shows the conditions in the post-column fluorescence detection method in this case.

TABLE 3

Conditions in chromatography and detection

| Detection method (Fluorescence) | Excitation light: 320 nm Fluorescence: 430 nm |
|---|---|
| Solution A | 20 mM Tris buffer (pH 7.2) |

TABLE 3-continued

| Conditions in chromatography and detection | |
| --- | --- |
| Solution B | 20 mM Tris Buffer (pH 7.2) 20 mM phosphate |
| Flow rate of mobile phase | 0.3 mL/min |
| Column temperature | 25° C. |
| Reagent solution | 20 mM Tris buffer (pH 7.2) 3 w/v % L-arginine |
| Injection rate of reagent solution | 0.2 mL/min |
| Temperature in the heater | 150° C. |

[Evaluation of the Result of Analysis]

Figure 2:
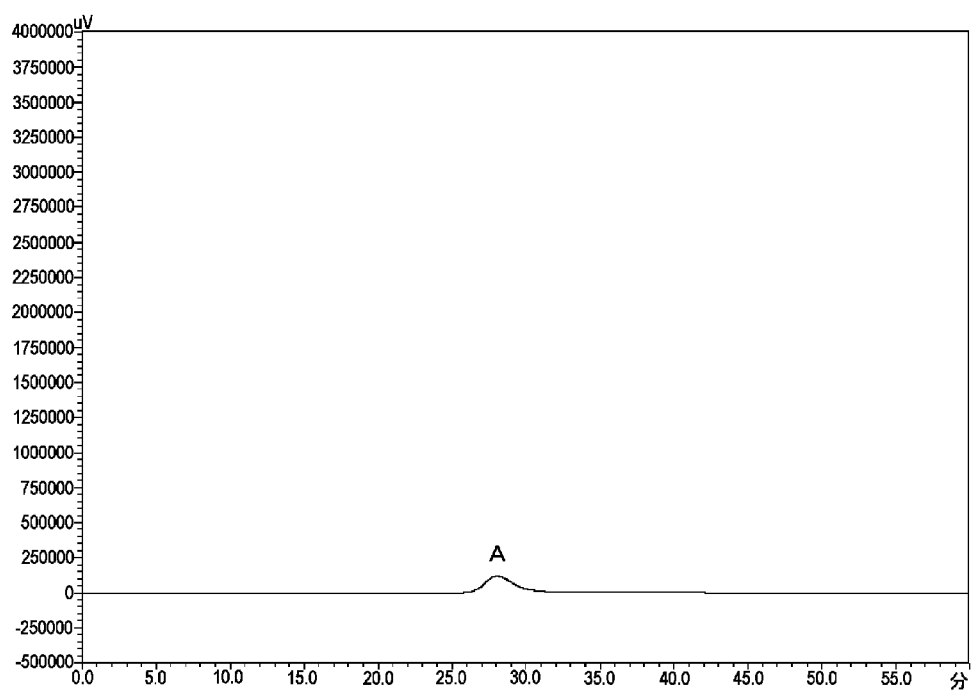
FIG. 2 is a chromatogram showing the result of analysis of the mannose-6-phosphate standard solution. The vertical axis represents fluorescence intensity (arbitrary unit), and the horizontal axis represents the length of time (minute) that lapsed after completion of loading of the reducing sugar standard solution.
Figure 3:
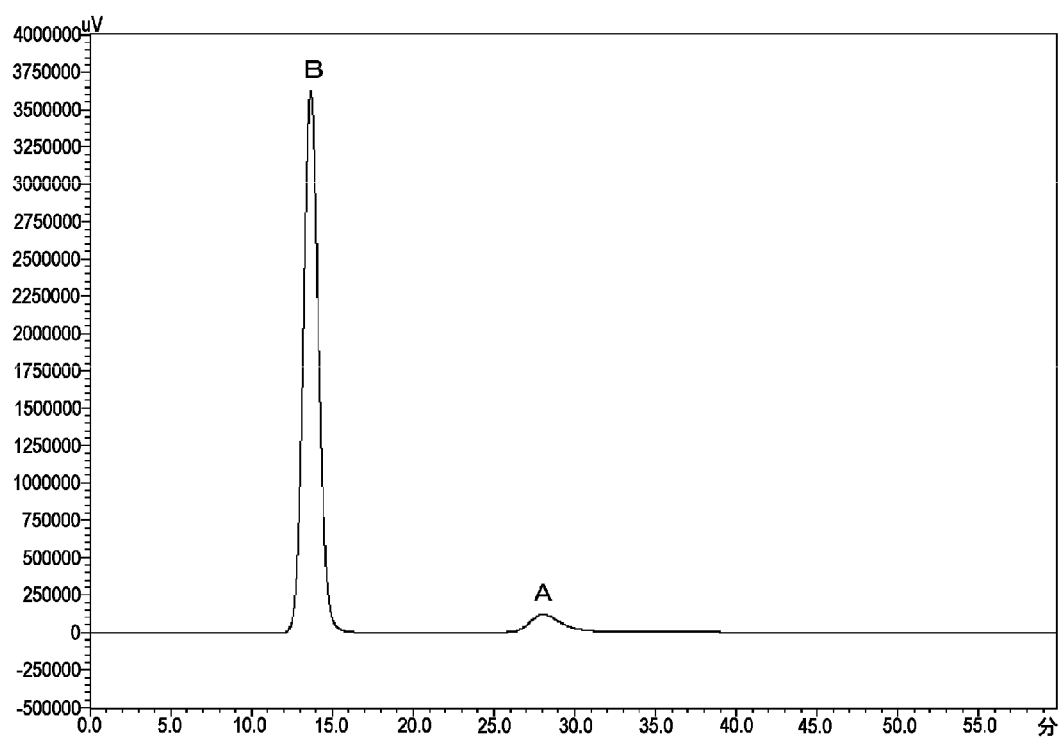
FIG. 3 is a chromatogram showing the result of analysis of the reducing sugar standard solution. The vertical axis and the horizontal axis are as in FIG. 2.

The result of the analysis of M6P Standard Solution is shown in FIG. 2. A peak attributed to mannose-6-phosphate sodium salt (Peak A) was obtained with such a clarity that permitted accurate calculation of the area of the peak (AUC).

[Analysis of Mannose-6-Phosphate by Post-Column Fluorescence Detection Method (2)]

Then, Reducing Sugar Standard Solution, instead of M6P Standard Solution, was analyzed using the same apparatus and following the same procedures as in the above sugar analysis (1).

[Evaluation of the Result of Analysis]

The result of the analysis of Reducing Sugar Standard Solution is shown in FIG. 2. After a peak (peak B) which was attributed to the mixture of the neutral sugars (mannose, fucose, and galactose) appeared, another peak (peak A) attributed to mannose-6-phosphate sodium salt appeared, completely separated from the former peak and with such a level of clarity that allowed accurate calculation of its area (AUC). The results indicate that mannose-6-phosphate can be analyzed by a post-column fluorescence detection method without using boric acid, by employing Tris buffer and a phosphate-containing Tris buffer as the mobile phases, and a hydroxyapatite column for liquid chromatography.

INDUSTRIAL APPLICABILITY

The present invention is useful as a method which enables detection of mannose-6-phosphate without using boric acid, which is toxic, in the post-column fluorescence detection method.

DESCRIPTION OF SIGNS

1: Autosampler
2: Thermostatic chamber (Column thermostatic chamber)
3: Column
4: Heater (Heat Block)
5: Cooling bath
6: Back-pressure generator
7: Fluorescence detector
A: Solution A
B: Solution B
C: Reagents solution

The invention claimed is:

1. An apparatus for separation analysis of mannose-6-phosphate contained in a sample using column chromatography, comprising: a column with a solid phase having affinity for phosphate, a flow path for an eluate from the column, a heater for heating the eluate in the flow path to cause mannose-6-phosphate and a basic amino acid contained in the eluate to react, a fluorescence detector installed in the flow path downstream of the heater for continuously irradiating the eluate with excitation light and measuring the intensity of fluorescence emitted from the eluate; and a back-pressure generator installed in the flow path between the heater and the fluorescence detector.

2. The apparatus for separation analysis according to claim 1, further comprising a cooling device installed between the heater and the back-pressure generator.

3. The apparatus for separation analysis according to claim 1, wherein the solid phase is selected from the group consisting of hydroxyapatite, fluoroxyapatite, and mixtures thereof.

4. A method for separation analysis of mannose-6-phosphate contained in a sample using the apparatus according to claim 1, comprising
loading a solution of the sample containing mannose-6-phosphate onto the column,
washing the column by passing through the column a sufficient amount of a first mobile phase consisting of a first buffer containing a predetermined concentration of at least one basic amino acid and adjusted to a predetermined pH,
eluting mannose-6-phosphate by continuously supplying, at a predetermined flow rate, a second mobile phase consisting of a second buffer containing at least one basic amino acid and a predetermined concentration of phosphate and adjusted to a predetermined pH,
continuously leading the eluate from the column to the flow path,
letting the eluate pass through the heater at a predetermined temperature over a predetermined length of time to heat the eluate, and
measuring and recording the intensity of fluorescence emitted from the eluate under irradiation with predetermined excitation light by subjecting the heated eluate to the fluorescence detector.

5. The method according to claim 4, wherein the pH of the first mobile phase is 5.5 to 9.5 and the pH of the second mobile phase is 5.5 to 9.5.

6. The method according to claim 5, wherein
the first buffer is selected from the group consisting of Tris buffer, Good buffer, acetate buffer, citrate buffer, citrate-phosphate buffer, phosphate buffer, glycine buffer, and carbonate buffer, or from a mixture solution of at least two of these, and
the second buffer is selected from the group consisting of Tris buffer, Good buffer, acetate buffer, citrate buffer, citrate-phosphate buffer, phosphate buffer, glycine buffer, and carbonate buffer, or from a mixture solution of at least two of these.

7. The method according to claim 4, wherein the concentration of the phosphate contained in the second mobile phase is 15-50 mM.

8. The apparatus for separation analysis according to claim 1, which further comprises in the flow path a supply channel for addition of a basic amino acid between the column and the heater.

9. The apparatus for separation analysis according to claim 8, further comprising a cooling device installed between the heater and the back-pressure generator.

10. The apparatus for separation analysis according to claim 8, wherein the solid phase is selected from the group consisting of hydroxyapatite, fluoroxyapatite, and mixtures thereof.

11. A method for separation analysis of mannose-6-phosphate contained in a sample using the apparatus according to claim 8, comprising loading the sample onto the column, washing the column by passing through the column a sufficient amount of a first mobile phase consisting of a first buffer adjusted to a predetermined pH, eluting mannose-6-phosphate by continuously supplying, at a predetermined flow rate, a second mobile phase consisting of a second buffer containing a predetermined concentration of phosphate and adjusted to a predetermined pH, continuously leading the eluate from the column to the flow path, continuously adding, at a predetermined flow rate, a solution containing at least one basic amino acid to the eluate in the flow path to form a mixture solution, letting the mixture solution pass through the heater at a predetermined temperature over a predetermined length of time to heat the mixture solution, and measuring and recording the intensity of fluorescence emitted from the mixture solution under irradiation with predetermined excitation light by subjecting the heated mixture solution to the fluorescence detector.

12. The method according to claim 11, wherein the pH of the first mobile phase is 5.5 to 9.5 and the pH of the second mobile phase is 5.5 to 9.5.

13. The method according to claim 12, wherein the first buffer is selected from the group consisting of Tris buffer, Good buffer, acetate buffer, citrate buffer, citrate-phosphate buffer, phosphate buffer, glycine buffer, and carbonate buffer, or from a mixture solution of at least two of these, and the second buffer is selected from the group consisting of Tris buffer, Good buffer, acetate buffer, citrate buffer, citrate-phosphate buffer, phosphate buffer, glycine buffer, and carbonate buffer, or from a mixture solution of at least two of these.

14. The method according to claim 11, wherein the concentration of the phosphate contained in the second mobile phase is 15-50 mM.

\* \* \* \* \*